United States Patent [19]

Ben-Bassat et al.

[11] Patent Number: 4,894,334

[45] **Date of Patent: * Jan. 16, 1990**

[54] METHOD OF IMPROVING THE YIELD OF HETEROLOGOUS PROTEIN PRODUCED BY CULTIVATING RECOMBINANT BACTERIA

[75] Inventors: Arie Ben-Bassat, Walnut Creek; Glenn Dorin, San Rafael; Keith Bauer, Oakland, all of Calif.

[73] Assignee: Cetus Corporation, Emeryville, Calif.

[ * ] Notice: The portion of the term of this patent subsequent to Apr. 7, 2004 has been disclaimed.

[21] Appl. No.: 35,069

[22] Filed: Apr. 6, 1987

Related U.S. Application Data

[63] Continuation-in-part of Ser. No. 594,250, Mar. 28, 1984, Pat. No. 4,656,132.

[51] Int. Cl.$^4$ ...................... C12P 21/00; C12N 15/00; C12N 1/38; C12N 1/20

[52] U.S. Cl. .................................. 435/69.1; 435/244; 435/247; 435/252.33; 435/172.3; 435/69.5; 435/69.51; 435/69.52; 935/38

[58] Field of Search .................... 435/172.3, 68, 240.1, 435/244, 247, 253, 70, 71, 252.33; 935/33, 38, 111

[56] References Cited

U.S. PATENT DOCUMENTS

| | | | |
|---|---|---|---|
| 4,499,188 | 2/1985 | Konrad et al. | 435/70 |
| 4,637,980 | 1/1987 | Auerbach et al. | 435/68 |
| 4,656,132 | 4/1987 | Ben-Bassat et al. | 435/68 |

FOREIGN PATENT DOCUMENTS 0036776 9/1981 European Pat. Off. .

OTHER PUBLICATIONS

L. O. Ingram, Journal of Bacteriology, Feb. 1976, pp. 670–678, vol. 125, No. 2.

Philip C. Lee et al., Proc. Natl. Acad. Sci., vol. 80, pp. 7496–7500 (1983).

*Primary Examiner*—Elizabeth C. Weimar
*Assistant Examiner*—Mary E. Pratt
*Attorney, Agent, or Firm*—Philip L. McGarrigle; Albert P. Halluin

[57] ABSTRACT

A method for improving the yield of heterologous protein such as ricin A toxin, produced by recombinant bacteria by supplementing the nutrient medium in which the bacteria are grown with an ethanol and/or amino acid mixture during the terminal phase of the cultivation. Also disclosed is a method for improving the yield of heterologous proteins under the control of the PL promoter.

9 Claims, 3 Drawing Sheets

METHOD OF IMPROVING THE YIELD OF HETEROLOGOUS PROTEIN PRODUCED BY CULTIVATING RECOMBINANT BACTERIA

This application is a continuation-in-part of U.S. application Ser. No. 594,250, filed March 28, 1984 now U.S. Pat. No. 4,656,132.

TECHNICAL FIELD

This invention is in the field of biochemical engineering. More particularly it relates to a process for cultivating heterologous protein-producing recombinant cells such that the yield of the heterologous protein is improved.

BACKGROUND ART

Synthetic and chemically defined media for cultivating microorganisms are well known. Conventional nutrient media for cultivating bacteria have been used to grow reconbinant bacteria that are capable of producing heterologous polypeptides. See, for instance, European patent application 81301227.5 (published under number 0036776 on 30 September 1981) and commonly owned Patent No. 4,499,188, issued February 12, 1985. Casamino acids have been included in such nutrient media throughout the cultivation period. Ethanol is known to have various effects on *E. coli* metabolism. See Ingram, L.O., *J. Bacteriol* (1976) 125:670–678 and Lee, P. C., et al, PNAS (USA) 80:7496–7500.

DISCLOSURE OF THE INVENTION

The invention concerns a method of improving the yield of heterologous protein produced by cultivating recombinant bacteria in a liquid nutrient medium comprising supplementing the medium with an effective amount of ethanol and/or a mixture of amino acids that support bacterial growth during the terminal portion of the cultivation.

MODES OF CARRYING OUT THE INVENTION

Figure 1:
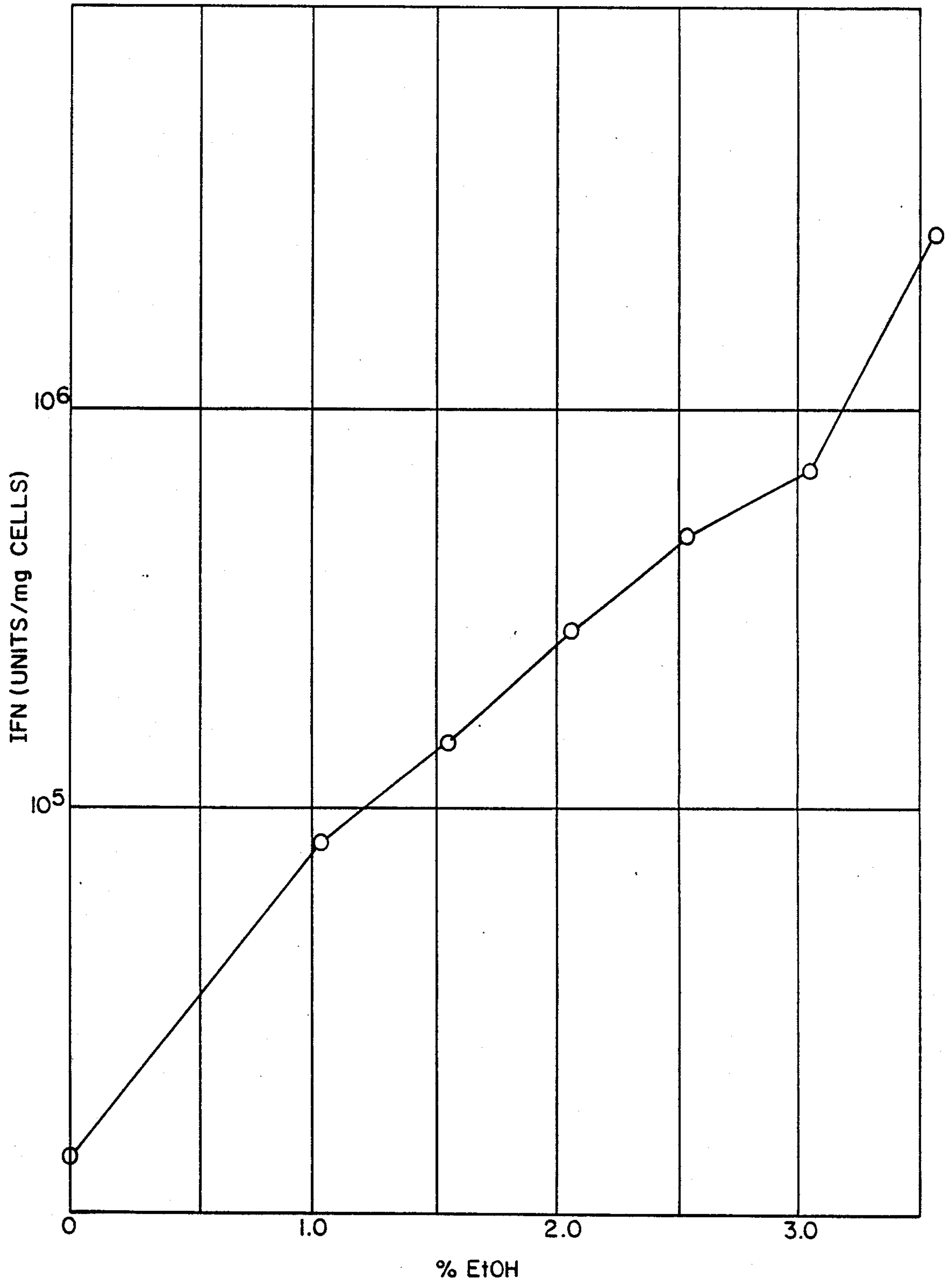
FIG. 1 is a graph of percent ethanol verus IFN-β activity showing the results of the experiments described in Example 1, infra.

As used herein, the term "heterologous" refers to polypeptides not produced by wild type bacteria. The heterologous polypeptides that are made by the invention process will typically have industrial, agricultural, or health care utility. In most instances, the polypeptides will be nonbacterial polypeptides that have amino acid sequences that are substantially identical to eukaryotic cell proteins or viral proteins. In this regard, the term "substantially identical" means that the amino acid sequences of the microbially produced synthetic polypeptide and the native polypeptide are either identical or differ by one or more amino acid alterations (deletions, additions, substitutions) that do not cause an adverse functional dissimilarity between the synthetic polypeptide and its native counterpart. Preferred hydrophobic polypeptides of 15–30 Kd have activity similar to the following:lymphokines, such as IFN-α,IFN-β, IFN-γ, CSF-M, CSF-G, CSF-GM, IL-1, IL-2, and IL-3; lymphotoxin and ricin A chain. For convenience, such polypeptides are referred to herein by their native designations (e.g., IFN-α, IFN-β, etc.) regardless of whether they are identical chemically to the native polypeptide.

The recombinant bacteria that are used in the invention may be made by recombinant DNA techniques. These techniques typically involve (i) cloning a synthetic structural gene or a structural gene of genomic origin that encodes the heterologous polypeptide into an appropriate plasmid or viral expression vector at a site which permits expression thereof (i.e., at a site controlled by a promoter-operator, a ribosome binding site for the translation of the transcribed mRNA, and a translation start codon in the same translational reading frame as the structural gene), (ii) introducing the vector into competent bacteria, and (iii) selecting recombinant cells (also called "transformants" ) either by a plasmid marker function or their ability to produce the heterologous polypeptide. *E. coli* or gram-negative bacteria that have metabolisms similar to *E. coli* are preferred. The heterologous polypeptide is generally present as an insoluble aggregate in the cytosol of *E. coli* transformants i.e., it is a nonsecreted polypeptide).

The heterologous polypeptide-producing transformants are cultivated in a liquid nutrient medium. The medium comprises an excess of conventional nutrient materials that fulfill the cellular growth requirements of the bacteria, thereby enabling the bacteria to grow and multiply to a predetermined cellular density. Such materials will include sources of carbon and nitrogen for synthesis of cellular components and energy, and minerals (ions) such as sulfur ($SO_4{}^{31\ 2}$), phosphorous ($PO_4{}^{31\ 4}$), $Mg^{+2}$, $K^+$, $Cu^{++}$, $Zn^{++}$, $Mn^{++}$ and $Fe^{++}$. While one or more amino acids may be added to the medium initially, the protein hydrolysate that is used to enhance yield is not present initially. Oxygen will also be provided to the medium. In order to achieve maximum cellular densities, the cultivation will usually be carried out in a manner that enhances the area of the oxygen-liquid interface.

The yield enchancement achieved by the invention method is particularly pronounced when a low inoculum concentration is used in the cultivation. In this regard, the inoculum concentration will typically be in the range of 0.1 to 10 mg per liter dry weight of cells, more usually about 0.1 to 1 mg per liter. Expressed in terms of inoculum volume per final volume of fermentation medium the inoculum concentration will usually be 0.1 to 10 v/v%, more usually 0.1 to 1 v/v%.

Important environmental factors affecting the cultivation include pH and temperature. The temperature will range between the minimum and maximum growth temperatures. Most bacteria exhibit maximum growth rate over a fairly narrow temperature range. For mesophilic bacteria, such as *E. coli,* the optimum temperature range is about 25° C. to about 42° C., preferably about 37° C. Most organisms will tolerate pH ranging over several pH units. For bacteria, such as *E. coli,* the tolerable pH lies in the range of about 6 to 8, with 6.8 being preferred.

Promoter DNA sequences can be used to control the expression of genes for heterologous proteins whereby the transcriptional activity of the gene can be activated at a predetermined level of cell growth. For example, if expression is under the control of the tryptophan (trp) promoter-operator, expression may be controlled by adding tryptophan to the medium. An excess of trypthophan may be added initially and then removed from the medium when the desired level of cellular growth has been achieved. Alternatively, tryptophan is added in a predetermined amount that is correlated to the volume of nutrient medium and the approximate amount of tryptophan that would theoretically be in the cell mass in the volume at the desired level of growth. In the presence of excess preferred carbon source, such as glucose, the bacteria will use the tryptophan in the medium rather than producing it themselves for use in the production of cellular protein. While added tryptophan is present the bacteria repress expression of the heterologous polypeptide under the control of the trp promoter-operator. By initially adding a proper amount of tryptophan to the media the bacteria may be grown to a predetermined cellular density with the trp operator repressed. Commonly owned U.S. Pat. No. 4,499,188 describes the process for bacterially producing heterologous polypeptides under the control of the trp promoter-operator.

As another example, the heterologous gene can be thermally induced when placed under the control of the bacteriophage λ PL promoter-operator and the *E. coli* lysogen, DG95λ ($\lambda N_7 N_{53}$cI857susPSO), or the bacteriophage λ replication deficient *E. coli* lysogen, DG116 (λcI857, bio$T_{761}$ ΔH1), is used as the expression host. These strains encode a temperature-sensitive λ cI repressor. At low temperature (30°-32° C.) the repressor is active to bind the PL promoter, repressing the heterologous gene. At elevated temperatures (36°-42° C.) the repressor is inactivated and no longer binds the PL promoter, thus allowing the heterologous gene to be expressed.

The ethanol and/or amino acid mixture are added to the nutrient medium during the terminal portion of the cultivation. The exact point in the cultivation at which these materials are added is not critical. In terms of the extent of bacterial growth, the ethanol and/or amino acid mixture will usually be added when the cellular density (as measured in optical density (OD) units by a spectrophotometer at 680 nm) is at least about 2 OD units, preferably at least about 10 OD units. In instances where the expression of the gene encoding the polypeptide has been repressed, it is preferred to add the ethanol and/or amino acid mixture during the expression phase of the cultivation (i.e. the phase following derepression of the operator through removal or thermal inactivation of the repressor). The duration of the growth period after the ethanol and/or amino acid mixture is added may vary depending upon the particular bacteria, heterologous polypeptide, and cultivation conditions. Its duration will normally be in the range of about 1 to 5 hours. The cellular density at harvest will usually be in the range of 10 to 40 OD units, more usually 20 to 40 OD units.

The amount of ethanol added will typically be in the range of about 0.5% to 5% (v/v), preferably 1% to 3%. Mixtures of amino acids for use in supplementing the bacterial growth media are available commercially. These mixtures are typically protein hydrolysates that are made by subjecting naturally occurring proteinaceous materials, such as casein, soybean meal, lactalalbumin, animal tissues, and gelatin, to acid or enzymatic digestion. Alternatively, mixtures of amino acids may be made up from pure amino acid stocks. When the expression of the gene is under the control of the trp promoter-operator, the mixture of amino acids should lack tryptophan. Acid-hydrolyzed casein lacks tryptophan and is accordingly preferred for such systems. The amount of amino acid mixture added to the nutrient medium will usually be in the range of about 0.5% to 5% (w/v), preferably 1% to 3%. The alkanol and amino acids may be added to the nutrient medium separately or combined.

After harvest, the cells are processed to recover the heterologous polypeptide. This processing will normally involve disrupting the cells, separating crude heterologous polypeptide from bacterial proteins via one or more extraction steps, solubilizing the polypeptide (depending upon its solubility and hydrophobicity) and further purifying the polypeptide by gel filtration, high performance liquid chromatography or other protein purification procedures. Human lymphokines such as IFN-β and IL-2 that are made by recombinant bacteria are preferably recovered from the cellular material in a reduced state and then oxidized to their native configuration.

Procedures for recovering and oxidizing IFN-β and IL-2 are described in commonly owned U.S. Pat. No. 4,450,103, issued May 22, 1984 and commonly owned U.S. Pats. No. 4,530,787 issued July 30, 1985 and 4,569,790, issued February 11, 1986.

The following examples further describe the materials and techniques used in carrying out the invention. These examples are not intended to limited the invention an any manner.

EXAMPLE 1: Effect of Ethanol on IFN-$\beta_{ser17}$ Production

IFN-$\beta_{ser17}$ is a microbially produced mutein of IFN-β in which the cysteine residue at amino acid position 17 is replaced with a serine residue. IFN-$\beta_{ser17}$ has two remaining cysteine residues: one at position 31 and the other at position 141. In native IFN-β the cysteines at position 31 and 141 interact to form a disulfide bridge. Commonly owned U.S. Pat. No. 4,518,584, issued May 21, 1985 describes the genetic engineering techniques that may be used to make genetically engineered *E. coli* that produce IFN-$\beta_{ser17}$. The disclosure of that patent is incorporated herein by reference to the extent necessary to satisfy 35 US §112.

The recombinant *E. coli* host, MM294-1, transformed with the plasmid pSY2501 (CMCC #1494, ATCC #39517) was used for the production of IFN-$\beta_{ser17}$. The IFN-$\beta_{ser17}$-producing *E. coli* (IFN-$\beta_{ser17}$/mm294-1) were grown in the following media:

| Ingredient | Approximate Initial Concentration |
|---|---|
| $Na_3$ Citrate.$2H_2O$ | 3 mM |
| $KH_2PO_4$ | 30 mM |
| $(NH_4)_2SO_4$ | 74 mM |
| $MgSO_4.7H_2O$ | 3 mM |
| $MnSO_4.H_2O$ | 46 μM |
| $ZnSO_4.7H_2O$ | 46 μM |
| $CuSO_4.5H_2O$ | 1-2 μM |
| L-tryptophan | 50 mg/liter |
| $FeSO_4.7H_2O$ | 74 μM |
| thiamine.HCl | 0.002% |
| glucose | 0.3% |

At late exponential phase inoculum from this culture (4%) was transferred to new flasks containing a similar medium minus tryptophan and with varying amounts of ethanol. At the end of growth (as estimated by turbidity readings), samples were taken for IFN-β activity using a standard cytopathic effect (CPE) assay. FIG. 1 shows the results of these tests. As shown, addition of 3% ethanol increases IFN-β activity about one and one-half log units.

Production IL-$2_{ser125}$ is a microbially produced mutein of human IL-2 in which the cysteine residue at amino acid position 125 is replaced with a serine residue. Commonly owned U.S. Pat. No. 4,518,584 describes the procedures that may be used to make *E. coli* that produce IL-2 or IL-$2_{ser125}$. The disclosure of that patent is incorporated herein by reference to the extent necessary to satisfy 35 US § 112.

The recombinant *E. coli* host, MM294-1, transformed with the plasmid pLW45 (CMCC #1995, ATCC #39626) was used for the production of IL-$2_{ser125}$. Frozen tubes of the IL-$2_{ser125}$-producing *E. coli* strain (pLW45/MM294-1) grown to 1-2 $OD_{680}$ in brain heart infusion medium +50 mg/1 L-tryptophan, 5 mg/1 tetracycline, were thawed and used to inoculate flasks of seed medium at 1% (v/v) level. The composition of the seed medium was:

Seed Medium

| | |
|---|---|
| $NH_4Cl$ | 10 mM |
| $KH_2PO_4$ | 21.9 mM |
| $Na_2HPO_4$ | 28.1 mM |
| $K_2SO_4$ | 9 mM |
| $MgSO_4$ | 0.2 mM |
| TK-9* | 0.1 ml/liter |

*TK-9: 30 mM $ZnSO_4$
30 mM $MnSO_4$
1 mM $CuSO_4$

Sterile Additions

| | |
|---|---|
| 50% Glucose | 4 ml/liter = 2 g/liter |
| 1% Thiamine HCl | 1 ml/liter = 10 mg/liter |
| 0.5% L-tryptophan | 1 ml/100 ml = 50 mg/liter |
| 4 mM $FeSO_4$ | 0.25 ml/100 ml = 10 μM |
| 1% tetracycline | 50 μl/100 ml = 5 mg/liter |

The seed cultures were shaken at 37° C. until an $OD_{680}$ of 0.5-1.5 was reached (about 6 hr). These seed cultures were used to inoculate the following cultivation medium in a 10 liter fermenter.

Cultivation Medium

| | |
|---|---|
| $(NH_4)_2SO_4$ | 150 mM |
| $KH_2PO_4$ | 21.6 mM |
| $Na_3$ Citrate | 1.5 mM |
| TK-9 | 2 ml/liter |

pH adjust to 6.5 with NaOH
Vol → 8.5 liter
Sterilize

Sterile Additions

| | Vol. Added | Conc. |
|---|---|---|
| 50% Glucose | 100 ml | 5 g/liter |
| 1% Thiamine HCl | 20 ml | 20 mg/liter |
| 0.5% L-tryptophan | 140 ml | 70 mg/liter |
| 0.2 M $FeSO_4$ | 5 ml | 100 μM |
| 0.5 M $MgSO_4$ | 60 ml | 3 mM |

-continued

| | Vol. Added | Conc. |
|---|---|---|
| 1% tetracycline* | 5 ml | 5 mg/liter |

(These are each added separately from the other sterile additions.)
pH Control: 5 N KOH (50% glucose feed linked)
*Tetracycline made fresh in 100% ethanol.

Just prior to inoculation the pH was brought to 6.8 and maintained there throughout the run, using 5N KOH. A 50% glucose solution was fed in conjunction with alkali demand to maintain the residual glucose at approximately 5-10 g/liter. The oxygen demand of the culture was met as follows: from the initial conditions of 350 rpm and no air sparging, the rpm was first ranged up to 1200, followed by increasing the airflow to 5 liter/min, followed by sparging oxygen, to keep the dissolved oxygen at about 40% of air saturation.

The amount of tryptophan added was sufficient to repress IL2 production until 8-10 $O.D._{680}$. Growth rate of the culture was about 0.6 to 0.7 hr-1. After that, high expression began, and the cells continued to grow at a reduced rate - 0.4-0.5 $hr^{-1}$) When an $O.D._{680}$ of 40-50 was reached, 20 g/liter s(267 ml/10 liter fermenter) ethanol was added. The cells were harvested 3 hr after ethanol addition (usually 19-29 hr after incubation).

As compared to control fermentations carried out without adding ethanol to the cultivation medium, addition of ethanol resulted in about a 2-fold increase in production of IL-2 or IL-$2_{ser125}$, as the case may be. Analysis of harvest samples from the fermentations showed that the average yield per 10 liter fermenter was 8.3 g IL-2 and 5.6 g IL-$2_{ser125}$.

EXAMPLE 3: Effect of Ethanol on IFN-α Production

IFN-α6L is a human alpha interferon that is produced by recombinant *E. coli.* It is the subject of commonly owned, copending application Ser. No. 409,123 filed August 18, 1982. The disclosure of that application is incorporated herein by reference to the extent necessary to satisfy 35 USC §112.

The recombinant *E. coli* host, MM294, transformed with the plasmid pGW21, (CMCC #1815, ATCC #39409) was used for the production of IFN-α6L. The IFN-α6L producing strain (pGW21/MM294-1) was grown in a cultivation medium supplemented with ethanol at a level of 30 g/liter cultivation medium using procedures similar to the cultivation in the absence of ethanol, the ethanol addition resulted in a ½ to 1 log increase in yield of IFN-α6L.

EXAMPLE 4: Effect of Ethanol and Casamino Acids (CAA) on IL-$2_{ser125}$ Production Frozen tubes of IL-$2_{ser125}$-producing *E. coli* (Example 2 ) were thawed and inoculated directly into four fermentation tanks (A, B, C, D) containing the following fermentation medium to a level of 2 mg cell dry wt/liter.

$(NH_4)_4SO_4$:150 mM
$KH_2PO_4$: 21.6 mM
$Na_3$ Citrate: 15.0 mM
TK9: 2 ml/liter
pH adjusted to 6.56 with 2.5N NaOH autoclaved Sterile Additions (post autoclave)

$MgSO_4$. $7H_2O$ : 3 mM
$FeSO_4$ : 100 μM
L-tryptopha : 14 mg/liter

Thiamine HCl : 20 mg/liter
Glucose : 5 g/liter
Tetracycline : 5 mg/liter

The operating pH of the fermenters was maintained with 5N KOH at 6.8. A 50% glucose feed was triggered by base addition requirements. Residueal glucose in the fermenters was maintained between 5-10 g/liter. Dissolved oxygen in the fermenters was maintained at 40% through agitation to a maximum of 1200 rpm, then through air sparging to a maximum of 2 liters per min. Oxygen sparging was then used to 4 liters per min.

CAA (a 20% stock solution of autoclaved amino acids) were added to the fermenter when the turbidity equaled about 10 O.D. Growth rate between 1 and 10 O.D. is typically about u =0.60 −0.70 $hr^{-1}$. Full induction with 14 mg/liter tryptophan occurs around 1-2 O.D. By the time the CAA were added to the fermenters, expression of IL-2 $_{ser125}$ was fully turned on.

One percent CAA was added to tank "A". To the rest of the tanks 2% CAA was added. No ethanol was added to either tank "A" or "B". Two percent ethanol was added to tank "C", and 3% ethanol was added to tank "D", approximately 2 hr after CAA addition (20 O.D.).

Optical density, activity, and IL-2 protein measurements were made at various stages of the fermentations. Culture protein was estimated from optical density, and IL-2 protein from gel scans of crude extracts. Specific activity for IL-2 was calculated by combining the activity data with the gel scans. For comparison, a harvest sample taken from a fermentation lacking CAA addition was run concurrently on the gel.

These measurement are reported in Table 1 below.

TABLE 1

| | O.D. | Total U/mg Protein | U/Ferm. | % Total Protein | g IL-2/ Ferm. | Specific Activity U/mg IL-2 |
|---|---|---|---|---|---|---|
| Tank A | | | | | | |
| 11.6 hrs | 6.6 | $4.498 \cdot 10^4$ | $9.353 \cdot 10^8$ | — | — | |
| 12.3 | 10.0 | $5.155 \cdot 10^4$ | $1.624 \cdot 10^9$ | 2.1 | 0.66 | $2.4 \times 10^6$ |
| 13.3 | 16.5 | $1.111 \cdot 10^5$ | $5.773 \cdot 10^9$ | 2.9 | 1.5 | $3.8 \times 10^6$ |
| 14.3 | 27.5 | $1.652 \cdot 10^5$ | $1.431 \cdot 10^{10}$ | 5.4 | 4.7 | $3.0 \times 10^6$ |
| 15.3 | 28.6 | $1.546 \cdot 10^5$ | $1.393 \cdot 10^{10}$ | 5.0 | 4.5 | $3.1 \times 10^6$ |
| 16.3 | 30.6 | $7.147 \cdot 10^4$ | $6.889 \cdot 10^9$ | 6.1 | 5.9 | $1.17 \times 10^6$ |
| Tank B | | | | | | |
| 11.6 | 7.55 | $2.824 \cdot 10^4$ | $6.717 \cdot 10^8$ | — | — | |
| 12.3 | 11.65 | $5.764 \cdot 10^4$ | $2.115 \cdot 10^9$ | 2.9 | 0.91 | $2.3 \times 10^6$ |
| 13.3 | 17.4 | $1.224 \cdot 10^4$ | $6.820 \cdot 10^9$ | — | — | |
| 14.3 | 26.2 | $2.306 \cdot 10^4$ | $1.903 \cdot 10^{10}$ | 7.0 | 5.8 | $3.3 \times 10^6$ |
| 15.3 | 32.8 | $4.054 \cdot 10^4$ | $4.188 \cdot 10^9$ | 5.9 | 6.1 | $6.87 \times 10^5$ |
| 16.3 | 36.2 | $1.2161 \cdot 10^5$ | $1.387 \cdot 10^{10}$ | 7.6 | 8.7 | $1.59 \times 10^6$ |
| Tank C | | | | | | |
| 11.6 | 6.3 | $5.343 \cdot 10^4$ | $1.060 \cdot 10^9$ | — | — | |
| 12.3 | 9.65 | $6.374 \cdot 10^4$ | $1.937 \cdot 10^9$ | 2.4 | 0.73 | $2.65 \times 10^6$ |
| 13.3 | 14.6 | $9.443 \cdot 10^4$ | $4.343 \cdot 10^9$ | — | — | |
| 14.3 | 19.7 | $2.067 \cdot 10^5$ | $1.283 \cdot 10^{10}$ | 7.1 | 4.4 | $2.92 \times 10^6$ |
| 15.3 | 22.5 | $6.186 \cdot 10^4$ | $4.384 \cdot 10^9$ | 9.4 | 6.6 | $6.64 \times 10^5$ |
| 16.3 | 24.2 | $2.474 \cdot 10^5$ | $1.886 \cdot 10^{10}$ | 9.0 | 6.9 | $2.73 \times 10^6$ |
| 17.3 | 28.0 | — | — | 8.6 | 7.6 | |
| Tank D | | | | | | |
| 11.6 | 5.95 | $4.374 \cdot 10^4$ | $8.20 \cdot 10^8$ | — | — | |
| 12.3 | 9.35 | $3.468 \cdot 10^4$ | $1.021 \cdot 10^9$ | 2.1 | 0.62 | $1.65 \times 10^6$ |
| 13.3 | 12.7 | $1.111 \cdot 10^5$ | $4.443 \cdot 10^9$ | — | — | |
| 14.3 | 16.5 | $2.221 \cdot 10^5$ | $1.155 \cdot 10^{10}$ | 5.4 | 2.8 | $4.13 \times 10^6$ |
| 15.3 | 22.0 | $2.067 \cdot 10^5$ | $1.432 \cdot 10^{10}$ | 10.6 | 7.3 | $1.96 \times 10^6$ |
| 16.3 | 23.0 | $1.730 \cdot 10^5$ | $1.253 \cdot 10^{10}$ | 8.1 | 5.9 | $2.12 \times 10^6$ |
| 17.3 | 24.9 | — | — | 10.6 | 8.3 | |
| 18.3 | 26.4 | — | — | 10.7 | 8.9 | |
| Comparison | 45 | — | — | 3.6 | 5.1 | |

As shown by the data in the table, the addition of CAA increased the yield of total protein from 3.6% to 7.6% (2% CAA) and 6.1% (1% CAA). Qualitatively, 2% CAA gives significantly more IL-2 than 1%. Also, addition of ethanol (tanks C and D) improves the production of IL-2 over fermentations without ethanol (A and B).

Figure 2:
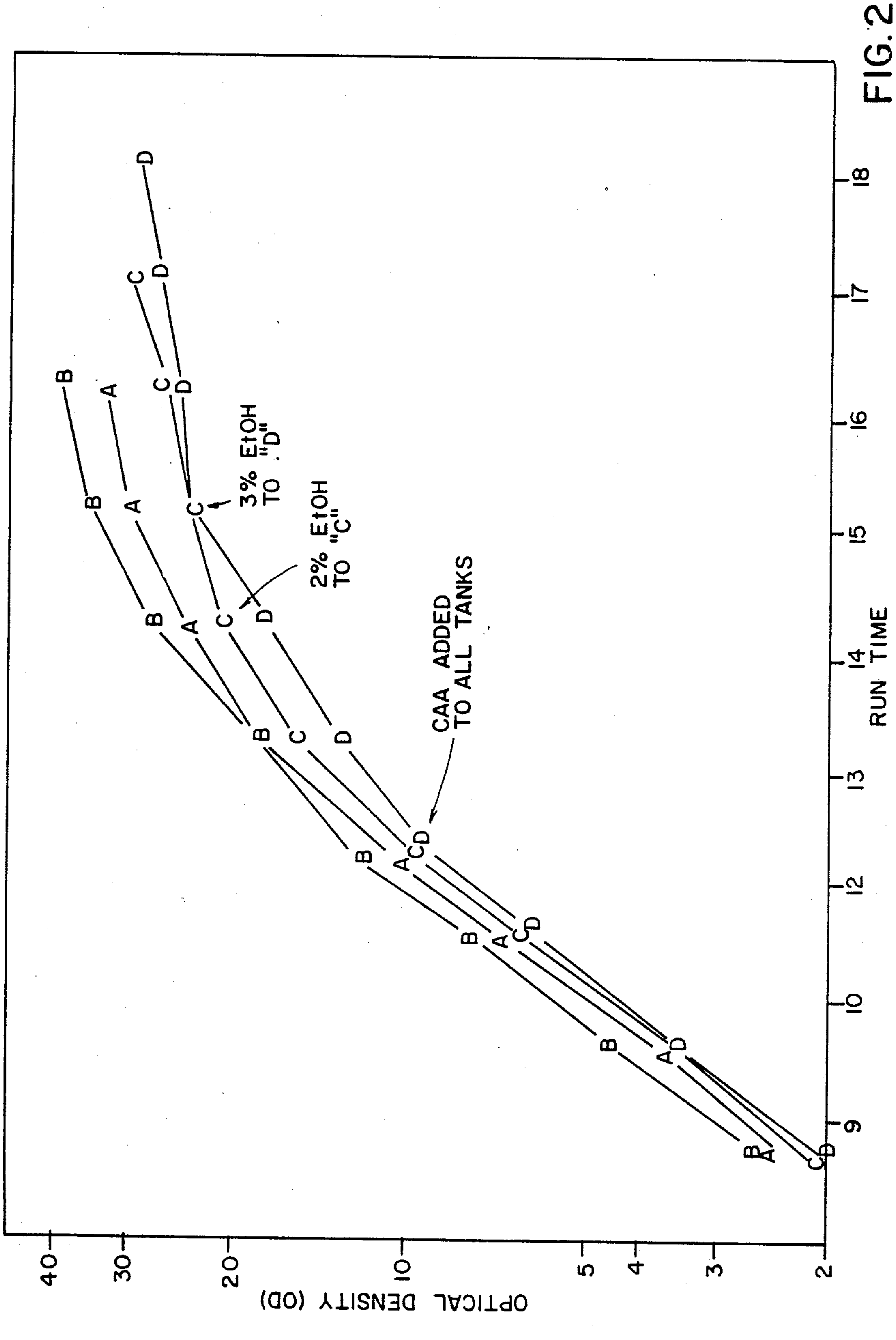
FIG. 2 is a graph of $OD_{680}$ versus run time for the fermentations described in Example 4, infra.

FIG. 2 shows the growth kinetics of the four fermentations.

EXAMPLE 5: Applying Casamino Acid Addition to the 1000 Liter Scale Fermentation of IL-$2_{ser125}$ The fermentation results at the 10-L level, shown in Example 4, were scaled up for the 1000 liter fermenter. The volume of the cultivation medium with its sterile additions were increased proportionally to obtain the identical concentrations as those at the 10 liter scale.

A seed culture of IL-$2_{ser125}$-producing *E. coli*, grown as described in Example 2 and frozen, was thawed and used to inoculate the 1000 liter fermentor. Growth was monitored periodically by measuring the culture's $OD_{680}$. The culture's pH was automatically controlled at 6.8, though the addition of 5M KOH. A 50% glucose feed was triggered by base addition requirements. The dissolved oxygen was controlled between 40-50%.

When the cultures $OD_{680}$ reached 13±1, a 20% stock of CAA was added to give a final concentration of 2% in the culture media. Full induction of IL-$2_{ser125}$ biosynthesis, due to limiting tryptophan, occurred by the time CAA's were added. The fermenter was run an additional 3.5 hrs. During this time the culture growth perameters were monitored and maintained automatically.

The cells were harvested and concentrated by crossflow filtration using a spiral cartridge. They were then disrupted by 3 passes through a homogenizer at about 6500 psi. After diafiltration versus deionized water, EDTA was added to a final concentration of 2 mM. To ensure that no viable recombinant organisms remained before containment was broken, 1L of octanol was also added to the fermenter. After several hours, the diafiltrate was again disrupted by one pass through the homogenizer followed by centrifugation. The pellet, containing insoluble IL-$2_{ser125}$ was stored as a paste at $-80°$ C. until subsequent purification.

The fermentation data of two separate 1000-L runs are shown in Table 2 to indicate the culture's parameters during the terminal stage of growth after the addition of CAA.

TABLE 2

IL-$2_{ser125}$ Production

Fermentor 1 Fermentation Run Data

| Run Time (hr) | Temp. °C. | pH | Dissolved Oxygen (%) | rpm | OD680 |
|---|---|---|---|---|---|
| 0 | 37 | 6.82 | 68 | 149 | NA |
| 14.0 | 37 | 6.80 | 38.3 | 286 | 10.3 |
| *14.5 | 36.8 | 6.80 | 43.2 | 296 | 14.0 |
| 15.0 | 37.1 | 6.80 | 36.0 | 290 | 16.8 |
| 16.0 | 37.0 | 6.80 | 24.4 | 287 | 23.7 |
| 17.0 | 36.9 | 6.81 | 36.0 | 284 | 30.8 |
| 17.5 | 36.9 | 6.81 | 32.4 | 290 | 33.2 |

Fermentor 2 Fermentation Run Data

| Run Time | Temp. °C. | pH | Dissolved Oxygen (%) | rpm | OD680 |
|---|---|---|---|---|---|
| 0 | 36.8 | 6.78 | 71.2 | 150 | NA |
| 12.5 | 37.1 | 6.80 | 41.6 | 178 | 4.1 |
| *13.5 | 37.1 | 6.79 | 41.2 | 239 | 7.5 |
| 14.2 | 37.1 | 6.79 | 40.4 | 275 | 10.9 |
| 14.5 | 37.0 | 6.80 | 40.3 | 285 | 12.0 |
| 15.5 | 37.1 | 6.80 | 33.6 | 262 | 15.8 |
| 16.5 | 37.1 | 6.80 | 41.2 | 297 | 23.1 |
| 17.5 | 37.1 | 6.81 | 39.6 | 297 | 27.5 |

*Casamino acid addition

The frozen paste from the 2-1000L fermenter runs were analyzed for total IL-$2_{ser125}$ recovery and % purity by SDS-PAGE electrophoresis, reverse phase-HPLC (RP-HPLC) and Lowry method of protein determination. Peak areas for IL-$2_{ser125}$ in the samples were compared to peak areas of a known concentration of purified IL-$2_{ser125}$ in order to determine IL-$2_{ser125}$ concentration in the sample. Results are shown in Table 3.

TABLE 3

| IL-$2_{ser125}$ Production | | | | | |
|---|---|---|---|---|---|
| | | SDS-PAGE | | RF-HPLC | |
| Fermentor Run | Total Protein (g) | Total IL-2 (g) | % Purity IL-2 | Total IL-2 (g) | % Purity IL-2 |
| 1 | 873.9 | 464.6 | 53.6 | 478.6 | 44.3 |
| 2 | 712.5 | 348.0 | 48.5 | 308.8 | 49 |

EXAMPLE 6: Effect of Casamino Acid on Ricin A Toxin (RTA) Production

Ricin A chain, RT-A, is a microbially produced peptide of the cytotoxic "A" subunit derived from castor bean seed ricin toxin. Commonly owned copending U.S. patent application Ser. No. 715,934 describes the procedures that may be used to make *E. coli* that produce ricin toxin A chain (RT-A). The disclosure of that patent application is incorporated herein by reference to the extent necessary to satisfy 35 US §112.

The recombinant *E. coli host, KB*-2, transformed with the plasmid pRAT1 (CMCC #2663) was used for the production of RT-A.A A frozen seed culture of the RTA producing strain (pRAT1/KB-2), grown to 1-2 $OD_{680}$ in brain heart infusion seed medium +50mg/1 L-tryptophan, 50mg/1 ampicillin and stored at $-70°$ C were thawed and used to inoculate flasks of seed medium at 1% (v/v) level. The composition of the seed medium was identical to that described in Example 2 except that in place of the sterile addition of 1% tetracycline, 1% ampicillin (made in sterile water) was added to a final concentration of 50mg/1.

The seed cultures were shaken at 37°C until an $OD_{680}$ of 0.35 was reached (about 8 hr). These seed cultures were used to inoculate two fermentation tanks (A&B) containing cultivation medium of the same composition as described in Example 2 except that in place of the sterile addition of 1% tetracycline, 1% ampicillin (made in sterile water) was added to a final concentration of 50 mg/l.

The operating pH of the fermenters was maintained with 5N KOH at 6.8. A 50% glucose feed was triggered by base addition requirements. Residual glucose in the fermenters was maintained between 5–10 g/l. Dissolved oxygen in the fermenters was maintained at 40% through agitation to a maximum of 1200 rpm, then through air sparging to a maximum of 2 liters per min. Oxygen sparging was then used to 4 liters per minute.

Casamino acid (CAA) (a 20% stock solution of autoclaved amino acids) were added to the fermenter when the turbidity equaled about $OD_{680}$of 10. Growth rate between 1 and 10 O.D. is typically about u=0.60–0.70 hr-1. Full induction with 14 mg/liter tryptophan occurs around 1–2 O.D. By the time the CAA were added to the fermenters, expression of RT-A was fully turned on. Two percent CAA was added to tank "A". Tank "B" was used as the control.

The fermenters were run for 17–18 hr after which time samples were analyzed for total RT-A production. Total protein was calculated from culture OD680. The percent RT-A was derived by subtracting the gel scan of crude extracts of the *E. coli* host (without the RT-A expressing plasmid) from the gel scans of the crude extracts from tanks A and B.

The results of the two experiments are shown in table 4.

TABLE 4

RT-A Induction ± CAA

| TANK | OD680 | TOTAL MG PROTEIN | PERCENT RT-A | TOTAL MG RT-A PROTEIN |
|---|---|---|---|---|
| A | 29.8 | 74500 | 8.3 | 6183 |
| B | 23.6 | 59000 | 2.6 | 1534 |

As shown by the table, the addition of 2% CAA increased the total mg of RT-A protein four fold.

Figure 3:
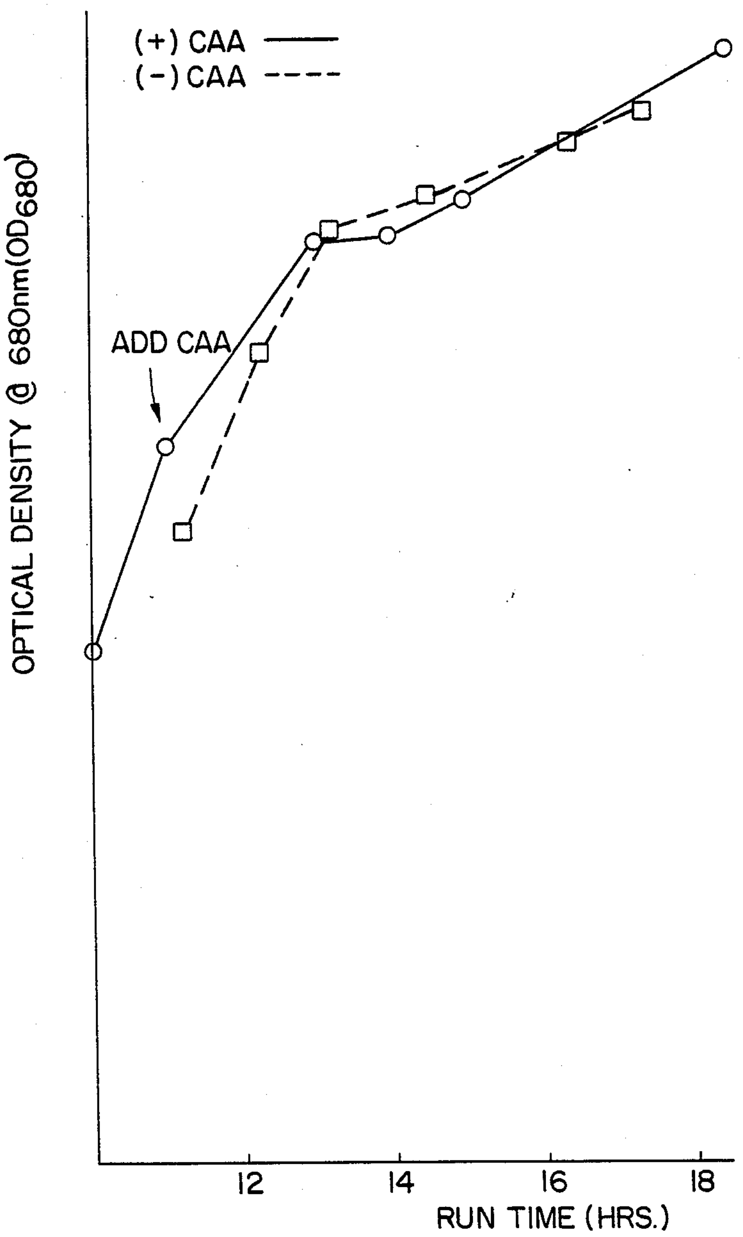
FIG. 3 is a graph showing the kinetics in using casamino acids in the production of Ricin A toxin protein.

FIG. 3 shows the growth kinetics for tanks A and B.

EXAMPLE 7: Effect of Casamino Acid (CAA) on Colony Stimulating Factor-1 Expression Colony stimulating factor-1 (CSF-1) is a lymphokine that induces the proliferation of certain cell types of the immune system, primarily macrophages. The isolation of the DNA sequence for human CSF-1, as well as its production by *E. coli,* are described in commonly owned, copending U.S. patent application Ser. No. 876,819. The disclosure of that patent application is incorporated herein by reference to the extent necessary to satisfy 35 US §112.

The microbial expression of CSF-1 is under the control of the PL promoter. As such, the production of CSF-1 protein can be repressed while growth of the culture is maintained at 30° C. Upon reaching a predetermined level of growth, the PL promoter can be derepressed by increasing the temperature to 42° C., which will in turn activate the production of CSF-1 protein. The addition of casamino acids (CAA), done simultaneously with the increase in temperature, is beneficial to the cells' production of CSF-1 as is illustrated with the following experiment.

The recombinant *E. coli* host, DG116, transformed with the plasmid pLCSFAsp59Gly15OTGA (CMCC #2946), was used for the production of CSF-1. A frozen seed culture of the CSF-1 producing strain (pLCSFAsp59Gly15OTGA/DG116), grown as described in Example 2 and frozen, was thawed and used to inoculate 20 mls of the same media +10 mM $FeSO_4$ and 50 μg/ml ampicillian. The initial $OD_{680}$ was 0.26. The culture was grown at 30° C. until an $OD_{680}$ of 0.8. From this culture, cells were taken to inoculate 20 mls of the following media: 1) seed media+10 mM $FeSO_4$+50 μg/ml ampicillian (control); 2) same as #1+0.5% CAA; and 3) same as #1 +2.0% CAA. The control received 4 mls of inoculum, and the others were inoculated with 2 mls each. The flasks were grown at 42° C. for 3 hours in a New Brunswick bench top incubator set to agitate at 250 rpm.

For analysis of CSF-1 expression, 20 mls of each were harvested by centrifugation and the milligrams of protein in each cell pellet was estiamated from the $OD_{680}$ at the time of harvest. The pellets were then resuspended in a volume to give an equivalent protein concentration for each of 2 mg/mls. Thirty microliters, or 60 μg, of the resuspended cells were then analyzed on an SDS-PAGE electrophoresis gel. The gel was stained with Coomassie Brilliant Blue and visually inspected.

The observed results, relative to the control, indicated the addition of 0.5% CAA and 2% CAA gave an approximately 2-fold and 4-fold increase in CSF-1 production, respectively.

EXAMPLE 8: Effect of Casamino Acid Addition (CAA) on Tumor Necrosis Factor Expression Tumor necrosis factor (TNF) is a lymphokine which is selectively necrotic to tumor cells, and neutral with respect to its reactions for normal tissue. The microbial production of TNF, as well as its muteins derived there from, are described in commonly owned, copending U.S. patent application Ser. Nos. 730,696, 760,661 and 792,815. The disclosure of these patent applications are incorporated herein by reference to the extent necessary to satisfy 35 US §112.

As with Example 7 and the expression of CSF-1, so too is the expression of TNF under the control of the PL promoter. As such, the thermal induction of TNF expression is achieved in a manner likened to that of CSF-1. The addition of casamino acids (CAA), done simultaneously with the increase in temperature to 42° C., has a beneficial effect on TNF production as is shown with the following experiment.

The recombinant *E. coli* host, DG95, transformed with the plasmid pAW740c (CMCC #2517, ATCC #53440), was used for the production of TNF. A frozen seed culture of the TNF producing strain (pAW740c/DG95), grown as described in Example 2 and frozen, was thawed and used to inoculate the same media+5 μg/ml tetracycline and grown overnight at 30° C. From this culture, cells were taken to inoculate 10 mls of the following media: (1) seed media +5 pg/ml tetracycline+0.5% glucose; and (2) same as 1 +2% CAA. The cultures were grown at 30° C. until $OD_{680}$ of approximately 1.0. TNF production was then induced by transferring 2 mls of the culture into 10 ml of identical media at 42° C. The cultures were grown for 5 hours at the elevated temperature.

For analysis of TNF mutein expression, the cultures' $OD_{680}$ were measured and 10 ml of each were harvested by centrifugation. The pelleted cells were resuspended to have an equivalent protein concentration of 2 mg/ml and analyzed using SDS-PAGE gel electrophoresis as described in Example 7.

The gel was stained with Coomassie Brilliant Blue and visually inspected.

The observed results, relative to the control, indicated that the addition of 2% CAA gave approximately a 3–5 fold increase in TNF production.

In addition, samples of *E. coli* were taken before and after thermal induction and assayed for TNF activity using the cytoxic assay procedure employing the L-929 assay system as described in commonly owned, copending U.S. patent application Ser. No. 730,695 (supra). The assay results, Table 5, show a 45% increase in TNF expression with 2% CAA present during induction, as compared to only a 5% increase when CAA are absent.

TABLE 5

TNF CYTOXICITY ASSAY RESULTS

| | Units TNF/mg Protein | | |
|---|---|---|---|
| | Pre Induction | Post Induction | % Increase |
| Cultivation Medium | $1.8 \times 10^5$ | $9 \times 10^5$ | 5 |
| Cultivation Medium + 2% CAA | $4 \times 10^4$ | $1.8 \times 10^6$ | 45 |

EXAMPLE 9: Applying Casamino Acid Addition to 100 Liter Scale Fermentation of Tumor Necrosis Factor (TNF)

The results of Example 8 were scaled up for the 100 liter fermenter. The volume of the cultivation medium with its sterile additions were increased proportionally to obtain the identical concentrations as those at the analytical scale.

A seed culture of TNF production *E. coli* strain pAW74Oc/DG95λ, grown as described in Example 2 and frozen, was thawed to 30° C., and inoculated into a 100 liter fermenter. The cells were grown at 30° C until an $OD_{680}$ of between 13–15 was obtained, approximately 24 hours, after which time the fermentation temperature was increased to 42° C. to induce the production of TNF. At the same time 20% CAA plus 0.5M MgSO4 were added to give a final concentration of 2% and 1.5 mM, respectively. To obtain optimal induction, the cells were grown 2.75 hrs. at 42° C.

The cellular broth was harvested by cross-flow filtration, using a spiral cartridge, followed with diafiltration against deionized water. The concentrated cell mass was then passed twice through a cell homogenizer at about 8000 psi. The disrupted cellular material was sequentially diafilrated using a cellulose ester membrane followed by a PTFE membrane. The majority of the TNF product passed through with the filtrates from each. The final filtrate was filter concentrated to between 3 and 5 liters and frozen at −70° C. to await further purification.

Table 6 givès the fermentation data of two separate 100 liter runs for the production of TNF. They indicate the cultures growth parameters during the thermal induction at 42° C. with the addition of casamino acids.

TABLE 6

TNF Production

Fermentor A
Fermentation Run Data

| Run Time | Temp. °C. | pH | Dissolved Oxygen (%) | rpm | OD680 |
|---|---|---|---|---|---|
| 0 | 30.0 | 6.80 | 94.7 | 75 | NA |
| 14.3 | 30.0 | 6.80 | 37.2 | 279 | 6.6 |
| 19.8 | 30.0 | 6.80 | 40.5 | 280 | 12.0 |
| 20.0 | 30.0 | 6.80 | 40.1 | 280 | 13.0 |
| *21.1 | 42.0 | 6.78 | 60.1 | 280 | 20.1 |
| 22.1 | 42.0 | 6.80 | 41.4 | 279 | 25.5 |
| 22.7 | 41.9 | 6.80 | 40.0 | 280 | 30.7 |

Fermentor B
Fermentation Run Data

| Run Time | Temp. °C. | pH | Dissolved Oxygen (%) | rpm | OD680 |
|---|---|---|---|---|---|
| 0 | 30.00 | 6.82 | 91.8 | 75 | NA |
| 19.5 | 30.00 | 6.80 | 39.0 | 279 | 10.1 |
| 20.0 | 30.00 | 6.80 | 39.1 | 279 | 12.2 |
| 20.2 | 30.00 | 6.80 | 39.5 | 279 | 13.1 |
| *21.2 | 42.00 | 6.78 | 37.0 | 278 | 19.6 |
| 22.2 | 42.00 | 6.78 | 37.5 | 279 | 32.8 |
| 23.0 | 42.00 | 6.78 | 38.6 | 279 | 35.2 |

*Temperature induction + CAA addition

The initial harvested cell mass from the two fermentor runs were further analyzed for total protein by the method of Lowry and total TNF by scans of SDS-PAGE electrophoresis gels having known concentrations of purified TNF as standards. The results are shown in Table 7.

TABLE 7

| Fermentor Run | [protein] (mg/ml) | TNF Production Total Protein (g) | [TNF] mg/ml | Total TNF |
|---|---|---|---|---|
| A | 5.56 | 523 | 0.87 | 82 |
| B | 6.83 | 656 | 0.72 | 69 |

Samples of the recombinant protein producing *E. coli* strains and the recombinant host *E. coli* strains disclosed herein were deposited in either the American Type Culture Collection (ATCC), 12301 Parklawn Drive, Rockville, Md 20851, USA, or the Cetus Main Culture Collection (CMCC), 1400 Fifty-Third Street, Emeryville, Calif. 94608. The deposit dates and asccession numbers for these samples are listed below.

Recombinant Protein Producing *E. coli*

| Protein Produced | Plasmid/Host | Deposit Date | CMCC # | ATCC # |
|---|---|---|---|---|
| IFN-$\beta_{ser17}$ | pSY2501/mm294-1 | 11/18/83** | 1865 | |
| IFN-$\alpha$6L | pGW21/mm294 | 8/10/83** | 1815 | 39409 |
| IL-$2_{ser125}$ | pLW55/mm294-1 | 11/18/83** | 1865 | 39516 |
| IL-$2_{ser125}$* | pLW46/mm294 | 9/26/83** | 1849 | 39452 |
| IL-$2_{ser125}$* | pLW45/mm294 | 3/6/84** | 1995 | 39626 |
| RT-A | pRAT1/KB-2 | 3/19/86 | 2663 | |
| TNF | pAW740c/DG95λ | 1/24/86** | 2517 | 53440 |
| CSF-1 | pLCSFAsp59Gly150TGA/DG116 | 4/7/87** | 2946 | 67383 |

Recombinant Host *E. coli*

| Name | Recombinant Host *E. coli* Deposit Date | CMCC # | ATCC # |
|---|---|---|---|
| mm294 | 2/14/84** | 1793 | 39607 |
| mm294-1 | 11/18/83** | 1872 | 39515 |
| DG95λ | 4/7/87** | 2141 | 53607 |
| DG116 | 4/7/87** | 2562 | 53606 |
| KB-2 | 3/29/85** | 2311 | 53075 |

*This portein also lacks the initial alanine of the native protein.
**ATCC deposit date.

The expression of the genes encoding IFN-$\beta_{ser17}$, IL-$2_{ser125}$, IFN-$\alpha$6L and RT-A in the recombinant bacteria described in Examples 1–6 is under the control of the trp promoter-operator. The expression of genes encodeing TNF and CSF-I in the recombinant bacteria described in Examples 7–9 is under the control of the PL promoter-operator.

Modification of the above-described modes for carrying out the invention that are obvious to those of skill in biochemical engineering and related fields are intended to be within the scope of the following claims.

We claim:

1. A method for improving heterologous protein yield from a recombinant *E. coli*, the method comprises:

inoculating a liquid nutrient medium with the *E. coli* and cultivating the *E. coli* at conditions which favor growth; and adding a composition to the *E. coli* culture when the culture's cellular density is at least 2 OD units when measured at 680 nm, the composition supports bacterial growth during the terminal portion of the cultivation and is absent from the liquid nutrient medium prior to the addition;

the composition comprises: from 0.5 to 5.0 v/v % ethanol; or from 0.5 to 5.0 w/v % of a protein hydrolysate or a mixture of amino acids; or mixtures thereof.

2. The method of claim 1 wherein the protein is a hydrophobic nonsecreted protein that has ricin A toxin.

3. The method of claim 1 wherein the inoculum concentration is 0.1 to 10 v/v %.

4. The method of claim 1 wherein the inoculum concentration is 0.1 to 1 v/v %.

5. The method of claim 1 wherein the ethanol or protein hydrolysate is added to the media when the optical density of the culture is at least 10.

6. A method for improving ricin A toxin yield from *E. coli* that are transformed with DNA encoding ricin A toxin, the DNA is under the control of the tryptophan operator-promoter the method comprises:

inoculating a liquid nutrient medium with the transformed *E. coli* into at an inoculum concentration from 0.1 to 1.0 v/v %;

cultivating the *E. coli* at conditions which favor growth; and adding from 0.5 to 5.0 w/v % acid hydrolyzed casein to the *E. coli* culture when the cellular density of the culture is at least 10 OD units when measured at 680 nm, the acid hydrolyzed casein is absent from the liquid nutrient medium prior to the addition.

7. A method for improving heterologous protein yield from a recombinant bacteriophage λ (c1857)*E. coli* lysogen, the heterologous protein is under the control of the bacteriophage λ PL promoter-operator, the method comprises:

inoculating a liquid nutrient medium with the *E. coli* lysogen at an inoculum concentration from 0.1 to 1.0 v/v % ;

cultivating the *E. coli* lysogen at conditions which favor growth; and adding from 0.5 to 5.0 w/v % acid hydrolyzed casein to the *E. coli* culture when the culture's cellular density is at least 10 OD units when measured at 680 nm and the λ PL promoter-operator is activated by elevating the culture temperature to 42° C., the acid hydrolyzed casein is absent from the liquid nutrient medium prior to the addition.

8. The method of claim 7 wherein the heterologous protein is selected from the group consisting of proteins having interferon-α (IFN-α) activity, interferon-β(IFN-β) activity, interferon-γ (IFN-γ ) activity, colony stimulating factor (CSF) activity, tumor necrosis factor (TNF) activity, and lymphotoxin activity.

9. The method of claim 7 wherein the heterologous protein is selected from the group consisting of colony stimulating factor-1 and tumor necrosis factor.

* * * * *